(12) United States Patent
Hasenoehrl

(10) Patent No.: US 10,437,266 B2
(45) Date of Patent: Oct. 8, 2019

(54) SYSTEMS FOR COUPLING THE OPERATIONS OF AN ENVIRONMENTAL MODIFYING UNIT AND A SMART APPLIANCE

(71) Applicant: The Procter & Gamble Company, Cincinnati, OH (US)

(72) Inventor: Erik John Hasenoehrl, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 69 days.

(21) Appl. No.: 15/684,375

(22) Filed: Aug. 23, 2017

(65) Prior Publication Data

US 2017/0351271 A1 Dec. 7, 2017

Related U.S. Application Data

(63) Continuation of application No. 14/879,112, filed on Oct. 9, 2015.

(51) Int. Cl.
*G05D 7/06* (2006.01)
*A61L 9/015* (2006.01)
(Continued)

(52) U.S. Cl.
CPC ............ *G05D 7/0635* (2013.01); *A61L 9/015* (2013.01); *A61L 9/032* (2013.01); *A61L 9/122* (2013.01); *A61L 9/127* (2013.01); *A61L 9/14* (2013.01); *F24F 3/16* (2013.01); *F24F 11/50* (2018.01); *G05B 15/02* (2013.01); *H04L 12/283* (2013.01); *H04W 4/80* (2018.02); *A61L 2209/11* (2013.01); *A61L 2209/111* (2013.01); *A61L 2209/132* (2013.01); *A61L 2209/135* (2013.01); *A61L 2209/16* (2013.01); *F24F 11/56* (2018.01);
(Continued)

(58) Field of Classification Search
CPC ............................... G05D 7/0635; F24F 11/50
USPC .................................................. 700/275–306
See application file for complete search history.

(56) References Cited

U.S. PATENT DOCUMENTS 5,924,597 A 7/1999 Lynn
6,267,297 B1 7/2001 Contadini et al.
(Continued)

FOREIGN PATENT DOCUMENTS

WO WO 2006/0126139 A1 11/2006
WO WO 2010/058382 A1 5/2010
(Continued)

OTHER PUBLICATIONS

Nakaizumi, Fumitaka, et al. "SpotScents: A novel method of natural scent delivery using multiple scent projectors." Virtual Reality Conference, 2006. IEEE, 2006.pp. 213-218 (Year: 2006).*
(Continued)

*Primary Examiner* — Satish Rampuria
(74) *Attorney, Agent, or Firm* — Andrew J. Hagerty; Abbey A. Lopez

(57) ABSTRACT

Systems for coupling the operations of an environmental modifying unit and a smart appliance are described. In one form the system includes a central communication unit, a baby monitor, and a dispenser for modifying the environment in which the baby monitor exists. The central communication unit, the baby monitor, and the dispenser are wirelessly connected to one another.

8 Claims, 5 Drawing Sheets

(51) Int. Cl.

| | |
|---|---|
| *H04W 4/80* | (2018.01) |
| *A61L 9/12* | (2006.01) |
| *A61L 9/14* | (2006.01) |
| *F24F 11/50* | (2018.01) |
| *F24F 11/56* | (2018.01) |
| *H04L 12/28* | (2006.01) |
| *G05B 15/02* | (2006.01) |
| *A61L 9/03* | (2006.01) |
| *F24F 3/16* | (2006.01) |
| *F24F 110/60* | (2018.01) |

(52) U.S. Cl.
CPC ... *F24F 2003/1689* (2013.01); *F24F 2110/60* (2018.01)

(56) References Cited

U.S. PATENT DOCUMENTS

| | | | |
|---|---|---|---|
| 7,154,579 | B2 | 12/2006 | Selander et al. |
| 7,469,844 | B2 | 12/2008 | Conway et al. |
| 7,786,889 | B2 | 8/2010 | Van Der Poel et al. |
| 8,170,405 | B2 | 8/2012 | Harris |
| 8,249,731 | B2 | 8/2012 | Tran et al. |
| 8,620,841 | B1 | 12/2013 | Filson et al. |
| 8,727,611 | B2 | 5/2014 | Huppi et al. |
| 8,886,785 | B2 | 11/2014 | Apte et al. |
| 8,892,261 | B2 | 11/2014 | Hoonhout et al. |
| 8,955,765 | B2 | 2/2015 | Porchia et al. |
| 9,113,052 | B1 | 8/2015 | Scalisi et al. |
| 9,115,908 | B2 | 8/2015 | Shetty et al. |
| 9,439,995 | B2 * | 9/2016 | Conroy ................. B05B 7/2416 |
| 9,452,234 | B2 * | 9/2016 | Conroy ................. B05B 7/2416 |
| 9,474,824 | B2 * | 10/2016 | Conroy ................. B05B 7/2416 |
| 9,691,214 | B2 * | 6/2017 | Chan ................... G07F 17/0014 |
| 9,804,398 | B2 * | 10/2017 | Watanabe ............... G09F 19/00 |
| 9,808,550 | B2 * | 11/2017 | Fantuzzi ................ A61L 9/122 |
| 10,258,713 | B2 * | 4/2019 | Becker .................... A61L 9/015 |
| 2003/0040813 | A1 | 2/2003 | Gonzales et al. |
| 2004/0163073 | A1 | 8/2004 | Krzyzanowski et al. |
| 2006/0161270 | A1 | 7/2006 | Luskin et al. |
| 2007/0166575 | A1 | 7/2007 | McLeod |
| 2008/0058740 | A1 | 3/2008 | Sullivan et al. |
| 2009/0265037 | A1 * | 10/2009 | Bassa ................. B60H 1/00771 700/276 |
| 2009/0271003 | A1 | 10/2009 | Can Houtert et al. |
| 2010/0196195 | A1 | 8/2010 | Moschel |
| 2011/0077758 | A1 | 3/2011 | Tran et al. |
| 2013/0081541 | A1 | 4/2013 | Hasenoehrl et al. |
| 2013/0082817 | A1 | 4/2013 | Gruenbacher et al. |
| 2014/0023060 | A1 | 1/2014 | Apte et al. |
| 2014/0188287 | A1 | 7/2014 | Sabata |
| 2014/0265920 | A1 | 9/2014 | Pederson |
| 2015/0019030 | A1 * | 1/2015 | Chandler ............. G05D 7/0629 700/283 |
| 2015/0030498 | A1 | 1/2015 | Ooten |
| 2015/0116110 | A1 | 4/2015 | Schuman |
| 2015/0160636 | A1 * | 6/2015 | McCarthy, III ........ G05B 15/02 348/552 |
| 2016/0151917 | A1 * | 6/2016 | Faridi .................... B25J 9/0003 700/253 |
| 2016/0195856 | A1 * | 7/2016 | Spero ..................... G06N 5/046 700/90 |
| 2016/0199977 | A1 * | 7/2016 | Breazeal ................ B25J 9/0003 700/246 |
| 2017/0102156 | A1 | 4/2017 | Hasenoehrl |
| 2017/0102159 | A1 | 4/2017 | Hasenoehrl |
| 2017/0102718 | A1 | 4/2017 | Hasenoehrl |

FOREIGN PATENT DOCUMENTS

| | | |
|---|---|---|
| WO | WO 2014/036133 A1 | 3/2014 |
| WO | WO 2014/040118 A1 | 3/2014 |
| WO | WO 2014/135990 A1 | 9/2014 |

OTHER PUBLICATIONS

Matsukura, Haruka, Tatsuhiro Yoneda, and Hiroshi Ishida. "Smelling screen: development and evaluation of an olfactory display system for presenting a virtual odor source." IEEE transactions on visualization and computer graphics 19.4 (2013): pp. 606-615. (Year: 2013).*
Bartelt, Robert J., and Bruce W. Zilkowski. "A versatile and quantitative volatile-delivery system for laboratory bioassays." Journal of chemical ecology 24.3 (1998): pp. 535-558. (Year: 1998).*
Ademoye, Oluwakemi A., and Gheorghita Ghinea. "Synchronisation of olfactory-enhanced multimedia: Perspectives from an empirical study." 2008 IEEE International Conference on Multimedia and Expo. IEEE, 2008.pp. 1425-1428 (Year: 2008).*
Tillotson, Jenny. "Scent by a Wireless Web." (2005).pp. 1-13 (Year: 2005).*
Gosain, Devashish, and Mohit Sajwan. "Aroma tells a thousand pictures: digital scent technology a new chapter in IT industry." Int. J. Curr. Eng. Tech 4 (2014): pp. 2804-2812. (Year: 2014).*
Yuan, Zhenhui, Gheorghita Ghinea, and Gabriel-Miro Muntean. "Quality of experience study for multiple sensorial media delivery." 2014 International Wireless Communications and Mobile Computing Conference (IWCMC). IEEE, 2014.pp. 1142-1146 (Year: 2014).*
Hughes, Ben, and Jenny Tillotson. "Design as a means of exploring the emotional component of scent." (2006).pp. 1-16 (Year: 2006).*
Murray, Niall, et al. "The impact of scent type on olfaction-enhanced multimedia quality of experience." IEEE Transactions on Systems, Man, and Cybernetics: Systems47.9 (2016): pp. 2503-2515. (Year: 2016).*
International Search Report PCTUS2016/055869, dated Dec. 21, 2016 (14 pages).
International Search Report PCTUS2016/055480, dated Dec. 19, 2016 (16 pages).
International Search Report PCTUS2016/055487, dated Dec. 13, 2016 (13 pages).

* cited by examiner

SYSTEMS FOR COUPLING THE OPERATIONS OF AN ENVIRONMENTAL MODIFYING UNIT AND A SMART APPLIANCE

CROSS REFERENCE TO RELATED APPLICATION

This application is a continuation of U.S. application Ser. No. 14/879,112, filed Oct. 9, 2015, the substance of which is incorporated herein by reference.

FIELD

The present disclosure is directed to a system and method for coupling the operations of a dispenser and a smart appliance.

BACKGROUND

Volatile composition dispensers exist in various forms, including non-energized devices that passively diffuse volatile compositions and energized devices that utilize energy in various forms to dispense, or assist in dispensing, a volatile composition. With volatile composition dispensers that include refills containing volatile composition, users can select from a variety of scents, and have the ability to replace a spent refill of one scent with a new refill of a different scent. Moreover, volatile composition dispensers exist that alternate delivery of different scents into the air. Users often prefer particular scents at certain times of the year, based upon the season or holiday. Users often have particular scents that they prefer while doing various tasks and activities around the house, including while cleaning, entertaining, and relaxing. There is a need for a volatile composition dispenser that is able to deliver a particular scent or different scents while a user is performing various tasks or activities while a home, in an office, or at a business.

SUMMARY

Aspects of the present disclosure include a system for delivering a volatile composition into the air, the system comprising a central communication unit capable of receiving incoming signals and sending outgoing instructions, the central communication unit communicably connected with a memory configured to store an algorithm. The system comprising a smart appliance communicably connectable with the central communication unit and configured to send incoming signals to the central communication unit alerting the central communication unit of a status of the smart appliance. The system further comprising a volatile composition dispenser that is communicably connectable with the central communication through a wireless communication link, wherein the algorithm controls the volatile composition dispenser using incoming signals sent from the smart appliance to the central communication unit.

Aspects of the present disclosure also include a method of delivering a volatile composition to at least one room with a volatile composition dispenser based on the status of a smart appliance within the same building, wherein the smart appliance and the volatile composition dispenser are each communicably connectable with a central communication unit through a wireless communication link, the method comprising the steps of: (a) turning on the smart appliance or starting a cycle on the smart appliance; (b) sending a first incoming signal to the central communication unit that alerts the central communication unit that the smart appliance is on or that the cycle has started; (c) sending a first outgoing instruction from the central communication unit to the volatile composition dispenser to turn on the volatile composition dispenser after the central communication unit receives the first incoming signal; (d) sending a second outgoing instruction from volatile composition dispenser freshening device after a set point is reached; and (e) optionally repeating steps (a) through (d).

DETAILED DESCRIPTION

While the methods and systems of the present disclosure will be described more fully it is to be understood at the outset of the description which follows that persons of skill in the appropriate arts may modify the methods and systems herein described while still achieving the favorable results of described in the present disclosure. Accordingly, the description which follows is to be understood as being a broad, teaching disclosure directed to persons of skill in the appropriate arts, and not as limiting upon the present disclosure.

The present disclosure includes systems and methods for coupling the operations of a volatile composition dispenser with the operation of a smart appliance. This may be beneficial to a user for a variety of reasons. For example, a user may desire for a room to have a particular smell as a particular appliance is running. In one instance, a user may desire that the smell of laundry detergent or fabric enhancer is dispensed into the air at the same that the washer and or dryer are operating. The volatile composition having the scent of a laundry detergent or fabric enhancer may be dispensed into the same room as the washer and dryer or may be dispensed into a different room so that a user can enjoy the scent in another location. Moreover, sometimes, a user may wish to have a particular scent in the air as the user is watching television or using another appliance to improve the television watching experience. By coupling the operation of the volatile composition dispenser and the operation of a smart appliance, a user may find a particular task or activity involving a smart appliance more desirable or satisfying.

The systems and methods include a central communication unit (CCU) that is communicably connectable one or more volatile composition dispensers and one or more smart appliances. The smart appliance may be a refrigerator, washer, dryer, dishwashers, microwave, stove, oven, garbage disposal, stereo, television, cable or satellite box, baby monitor, vacuum cleaner, security system, light, garage door opener, doorbell, indoor or outdoor sprinkler or irrigation system, and the like.

Figure 1:
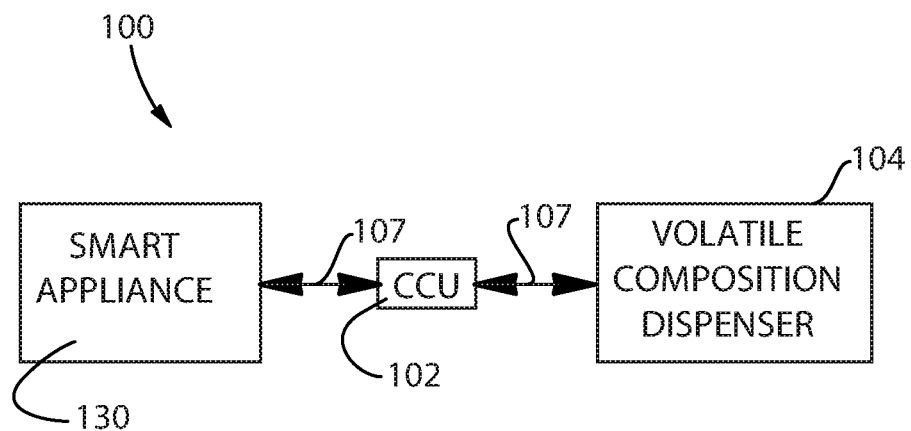
FIG. 1 illustrates exemplary components of a system, including the central communication unit, a volatile composition dispenser and a smart appliance that each communicate with the CCU through a wireless communication link.

FIG. 1 illustrates exemplary components of a system 100, including the central communication unit 102, a volatile composition dispenser 104 and a smart appliance 130 that each communicate with the CCU 102 through a wireless communication link 107.

For example, the CCU 102 may run an algorithm that turns ON the volatile composition dispenser 104 for at least a portion of the time that a smart appliance 130 is also turned ON or currently running. For example, the CCU 102 may be configured send an outgoing instruction to the volatile composition dispenser 104 to turn on the volatile composition dispenser 104 when an appliance turns ON or OFF or when a particular cycle of an appliance begins or ends. Then, either before, during, or after the smart appliance 130 is turned off, the CCU 102 may send an outgoing instruction to the volatile composition dispenser 104 to turn OFF the volatile composition dispenser 104.

As discussed in more detail below, the CCU comprises a memory that is capable of storing set points and algorithms and a processor that is capable of running algorithms and accessing the stored set points from the memory. The CCU is capable of running algorithms that couple the ON/OFF controls of the volatile composition dispenser with the ON/OFF controls or the particular cycles START or END times of one or more smart appliances. Various algorithms may be programmed depending upon the desired sequence of operations and the desired timing of each sequence.

Figure 2:
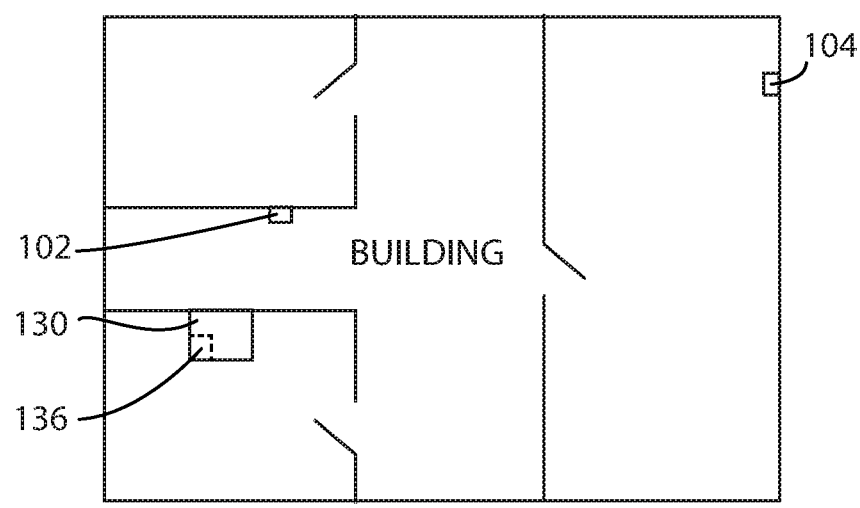
FIG. 2 illustrates a volatile composition dispenser placed in a different room than a smart appliance and CCU.

The volatile composition dispenser 104 may be placed in any room of a building. With reference to FIG. 2, the volatile composition dispenser 104 may be placed in a different room from the placement of the smart appliance 130 and may be placed in a different location than the CCU 102. However, it is to be appreciated that the volatile composition dispenser 104 may be placed in the same room as the smart appliance 130. The CCU may also be disposed in the same or different rooms from the volatile composition dispenser 104 or smart appliance 130. The volatile composition dispenser 104 may be moved to different rooms at the user's convenience.

Volatile Composition Dispenser

A volatile composition dispenser 104 may be used for the delivery of a volatile composition to the atmosphere or onto an inanimate surface. Such volatile composition dispenser 104 may be configured in a variety of ways. The volatile composition dispenser may include a wireless communication module 114 in order to establish a wireless communication link 107 with various components of the system 100. The volatile composition dispenser may additionally include mesh network border router functionality.

For example, the volatile composition dispenser 104 may be configured for use as an energized dispenser (i.e. powered by electricity; or chemical reactions, such as catalyst fuel systems; or solar powered; or the like). Exemplary energized volatile composition dispensers include a powered delivery assistance means which may include a heating element, a piezo element, thermal ink jet element, fan assembly, or the like. More particularly, the volatile composition dispenser may be an electrical wall-plug volatile composition dispenser, a non-limiting example of an electrical wall-plug volatile composition dispenser is described in U.S. Pat. No. 7,223,361; a battery (including rechargeable battery) powered volatile composition dispenser having a heating and/or fan element. In energized devices, the volatile material delivery engine may be placed next to the powered delivery assistance means to diffuse the volatile material. The volatile material may be formulated to optimally diffuse with the delivery assistance means.

The volatile composition dispenser 104 may be configured for use as a non-energized dispenser. An exemplary non-energized volatile composition dispenser includes a reservoir and, optionally, capillary, wicking means, or an emanating surface, to help volatile materials passively diffuse into the air (i.e. without an energized means). A more specific example a volatile composition dispenser includes a delivery engine having a liquid reservoir for containing a volatile material and a microporous membrane enclosing the liquid reservoir as disclosed in U.S. Pat. Nos. 8,709,337 and 8,931,711.

The volatile composition dispenser 104 may also be configured for use as an aerosol sprayer or a non-aerosol air sprayer. The volatile composition dispenser 104 can be programmed to automatically deliver a volatile composition to the atmosphere.

The volatile composition dispenser 104 may be configured in the form of an air purifying system to deliver both purified air and/or volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

The volatile composition dispenser 104 may be movable to different rooms within a housing or building. Moreover, a house or building may include one or more volatile composition dispensers that are positioned in the same room or in different rooms.

The volatile composition dispenser 104 may be able to contain and keep separated more than one volatile composition, including at least two different volatile compositions, or at least two different volatile compositions, or at least three volatile compositions. In such an instance, a volatile composition dispenser 104 may be configured to deliver one volatile composition having a scent that is meant to pair with one smart appliance and may also be configured to deliver a second volatile composition having a scent that is meant to pair with a second, different smart appliance.

Volatile Composition

The volatile composition may be an air freshening composition, including a perfume composition and/or a malodor control composition. The volatile composition may be an insect repellant.

The volatile composition may comprise volatile materials. Exemplary volatile materials include perfume materials, volatile dyes, materials that function as insecticides, essential oils or materials that acts to condition, modify, or otherwise modify the environment (e.g. to assist with sleep, wake, respiratory health, and like conditions), deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

The volatile composition may include perfume ingredients to provide a desirable scent in the air. The volatile composition includes a mixture of volatile aldehydes that are designed to deliver genuine malodor neutralization (and not function merely by covering up or masking odors). A genuine malodor neutralization provides a sensory and analytically measurable (e.g. gas chromatograph) malodor reduction. Thus, if the volatile composition delivers genuine malodor neutralization, the volatile composition will reduce malodors in the vapor and/or liquid phase. The volatile composition may comprise a mixture of volatile aldehydes that neutralize malodors in vapor and/or liquid phase via chemical reactions. Such volatile aldehydes are also called reactive aldehydes. Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase.

The volatile composition may include various other ingredients, including, but not limited to: surfactants; acid catalysts; polymers; buffering agents; solubilizers; antimicrobial compounds; preservatives; wetting agents; aqueous carrier; diluents; the like; and combinations thereof.

The volatile composition may be configured to have a scent that matches a scent associated with a particular smart appliance. For example, the volatile composition may have a baby powder scent in an instance where the volatile composition dispenser is associated with a baby monitor or other device located within a baby's room. In another example, the volatile composition may have a laundry detergent or fabric softener scent in an instance where the volatile composition dispenser is associated with the operation of a washer or dryer.

Smart Appliances

Various different smart appliances may also be connected with the system and included in the methods of the present disclosure. The smart appliances 130 may be communicably connectable with the CCU. With reference to FIG. 2, the smart appliance 130 may include a wireless communication module 136 in order to communicate with the CCU and/or volatile composition dispenser 104. Smart appliances may include refrigerators, washers, dryers, dishwashers, microwaves, stoves, ovens, garbage disposal, stereos, televisions, cable or satellite boxes, baby monitors, vacuum cleaners, security systems, lights, garage door openers, doorbell, indoor or outdoor sprinklers or irrigation systems, and the like.

The CCU may also be configured to control the volatile composition dispenser based upon the current status of a smart appliance. The smart appliances may be configured to send an alert in the form of an incoming signal to the CCU, alerting the CCU that a particular smart appliance has been turned on, turned off, or that a cycle of a smart appliance has started or ended. The smart appliance may also include sensors that are configured to send incoming signals to the CCU that alert the CCU as to current status of the smart appliance.

The CCU may also be configured initiate an algorithm that may include controlling a smart appliance based on sensor measurements sent to the CCU from other components of the system.

Sensors

One or more components of the system 100 may include a sensor 106. For example, the volatile composition dispenser 104, the CCU 102, an air handling device, or a smart appliance 130 may include one or more sensors 106. The sensors 106 may be configured to sense temperature, relative humidity, air quality, $CO_2$ levels, air particle counters, allergens and other air borne entities that have effect on human health, or the status of a component. The sensor 106 may include a wireless communication module in order to be communicably connectable with the CCU and various components of the system through a wireless communication link.

The sensor 106 may be powered by a power source 118. The sensor 106 may be powered independently from the volatile composition dispenser 104 or through the same power source of the volatile composition dispenser 104. The sensor 106 may be powered by a battery independently from the volatile composition dispenser 104 or by a battery configured to also power the volatile composition dispenser 104. The volatile composition dispenser and/or the sensor 106 may be powered through an electrical outlet. Battery power is used when the volatile composition dispenser is a mobile device that can be moved around from room to room or surface to surface. Moreover, a battery may be used to power the sensor 106 when the volatile composition dispenser is configured as a non-energized device that passively diffuses volatile compositions into the air.

The sensor is configured to send sensor measurements to the CCU in the form of incoming signals. The sensor measurements can be used in a variety of ways. For example, the sensor measurements may be viewed as live data; compared with set points, such as temperature set points in order to control the air handling device; or stored in a database for further analysis to recommend optimum set points taking comfort and energy efficiency into consideration.

Figure 3:
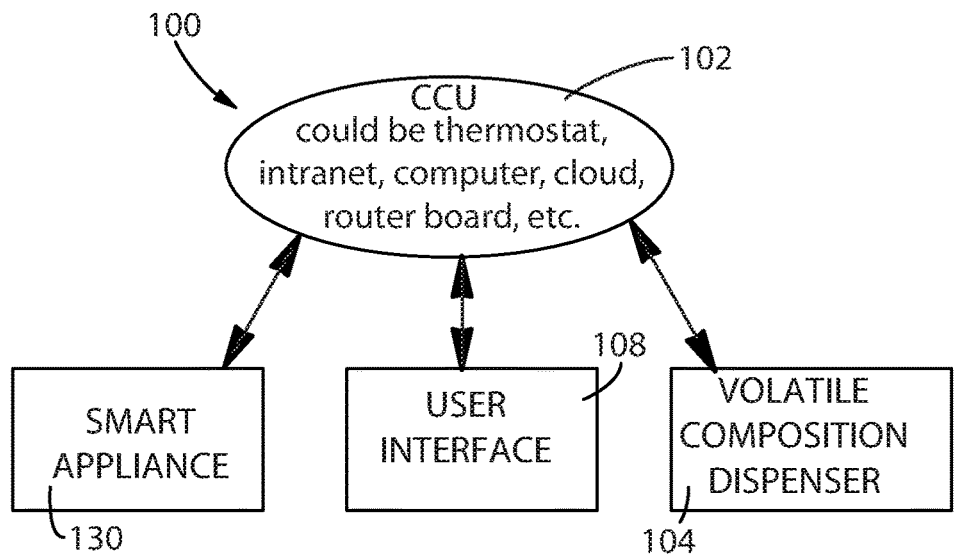
FIG. 3 depicts multiple possible flows of signals from the components to the CCU.

FIG. 3 depicts multiple possible flows of signals from the components to the CCU. Sensor measurements can flow from a component through the CCU to a user interface for live local sensor measurements. Alternatively, the sensor measurements can also pass from the sensor through the CCU to a destination server on the internet where it is stored in memory or analyzed by a processor in order to send instructions to the various components, including, but not limited to, the air handling device 110 and volatile composition dispenser 104.

Central Communications Unit

The CCU 102 can be configured in various different ways. The CCU 102 may be configured to receive incoming signals from the one or more components of the system 100 and send outgoing instructions to one or more components of the system 100, for example the smart appliance(s) and/or the volatile composition dispenser(s).

Figure 4:
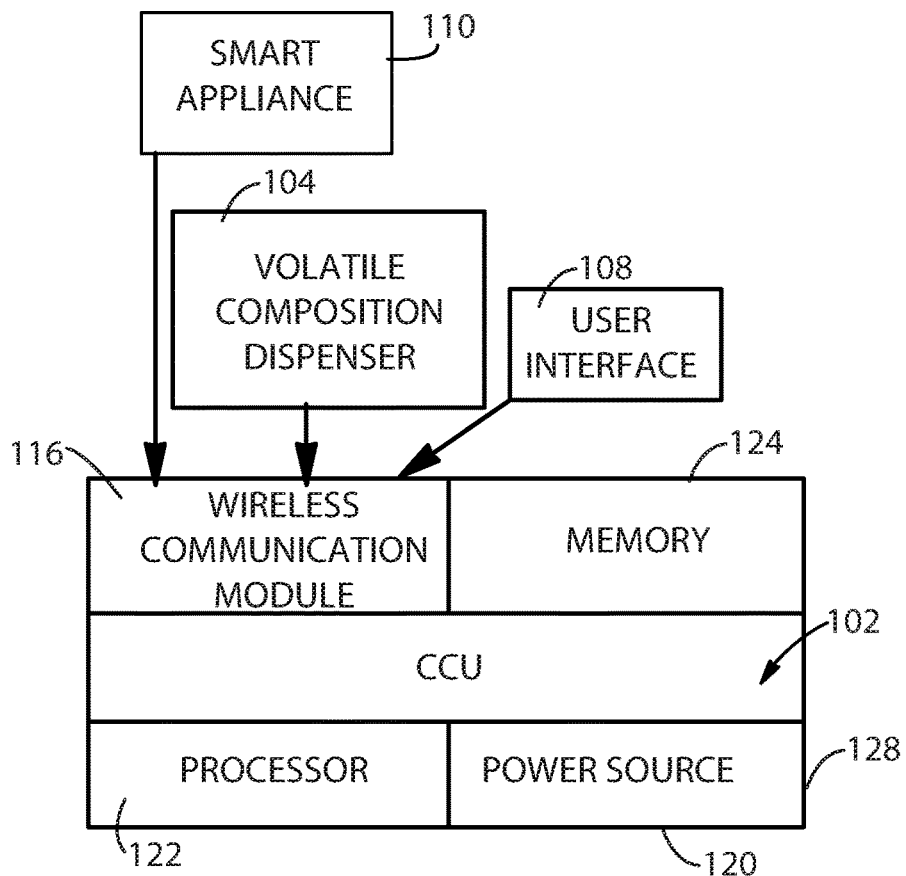
FIG. 4 illustrates an exemplary CCU having the processor and the memory disposed within a housing 12.

With reference to FIG. 4, the CCU 102 may be communicably connectable with various components of the system 100, including the sensor(s) 106, user interface(s) 108, the volatile composition dispenser 104, and/or smart appliances 130 using a wireless communication link 107. Various wireless communication links may be used, including 802.11 (Wi-Fi), 802.15.4 (ZigBee, 6LoWPAN, Thread, JennetIP), Bluetooth, combinations thereof, and the like. Connection may be through an ad hoc Mesh Network protocol. The CCU 102 may include a wireless communication module 116 in order to establish a wireless communication link 107 with the CCU 102 with various components of the system. Any module known in the art for establishing the communication links can be utilized.

The CCU 102 may comprise a processor 122. The processor 122 may be configured and programmed to carry out and/or cause to be carried out the one or more advantageous functionalities of the system 100 described herein. The processor 122 may be physically disposed within a CCU 102 or may be remotely located on a computer, special computer, smart device such as a phone or tablet, server, intranet, border router, cloud-based system, the like, or combinations thereof. The processor 122 can carry out algorithms stored in local memory; special-purpose processors or application-specific integrated circuits; algorithms carried out or governed remotely by central servers, or cloud-based systems, such as by virtue of running a Java virtual machine that executes instructions provided from a cloud server using Asynchronous JavaScript and XML or similar protocols.

The CCU 102 may comprise a memory 124. The memory may be configured to store set points; incoming signals, such as sensor measurements and status indicators; algorithms; and the like. The memory may be a local memory within the CCU 102 such as a flash drive, hard drive, read only memory, or random access memory. Or, the memory may be configured as remote memory on a computer, smart device such as a phone or tablet, on a server, or on cloud-based system. The memory 124 can be accessible to the processor 122 in a variety of ways.

The processor and/or the memory of the CCU 102 may be disposed within a housing of the CCU 102. The CCU 102 may be connected with or separate from various components of the system 100. For example, the CCU 102 may be physically connected with the smart appliance 130 or the volatile composition dispenser 104. The CCU 102 may be permanently positioned in a building in a separate room or location from other components such as the smart appliance 130, the volatile composition dispenser 104, and/or an air handling device, for example.

The CCU may include a clock or may be communicably connectable with a clock on a computer, smart device, or on the internet.

FIG. 4 illustrates an exemplary CCU 102 having the processor 122 and the memory 124 disposed within a housing 128. The CCU 102 shown in FIG. 5 may be disposed on or within a volatile composition dispenser 104, an air handling device 110, and/or a smart appliance. While FIG. 4 illustrates a processor 122 and a memory 124 disposed within the housing 128, it is to be appreciated that the processor 122 and/or the memory 124 may be remotely located relative to the CCU 102.

Incoming signals may pass through a CCU unit comprising a transmitter that transmits the incoming signals to the remote memory. Incoming signals may also be directly received by a component that is wirelessly communicating with the component sending the signals.

Figure 5:
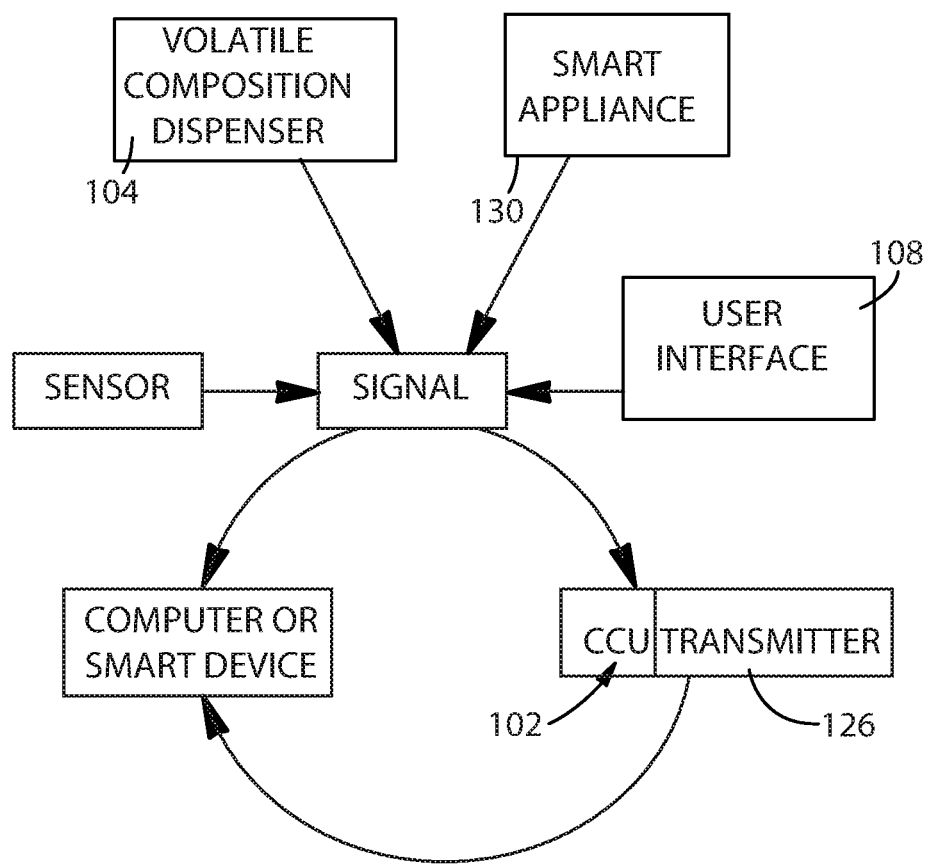
FIG. 5 illustrates multiple exemplary flows of incoming signals from various components of the system to a remote memory.

FIG. 5 illustrates multiple exemplary flows of incoming signals from various components of the system 100 to a remote memory. The incoming signals may flow directly from the smart appliance 130, volatile composition dispenser 104, or various other components to a computer or smart device through a wireless communication link or through a transmitter of the CCU to a remote memory. The processor 122 may access the incoming signals from the memory 124. The processor 122 may access the memory 124 through a wired or wireless communication link.

The processor 122 may be configured to compare incoming signals to set points stored in the memory 124. The processor is able to retrieve stored set points from the memory 124 to compare.

Figure 6:
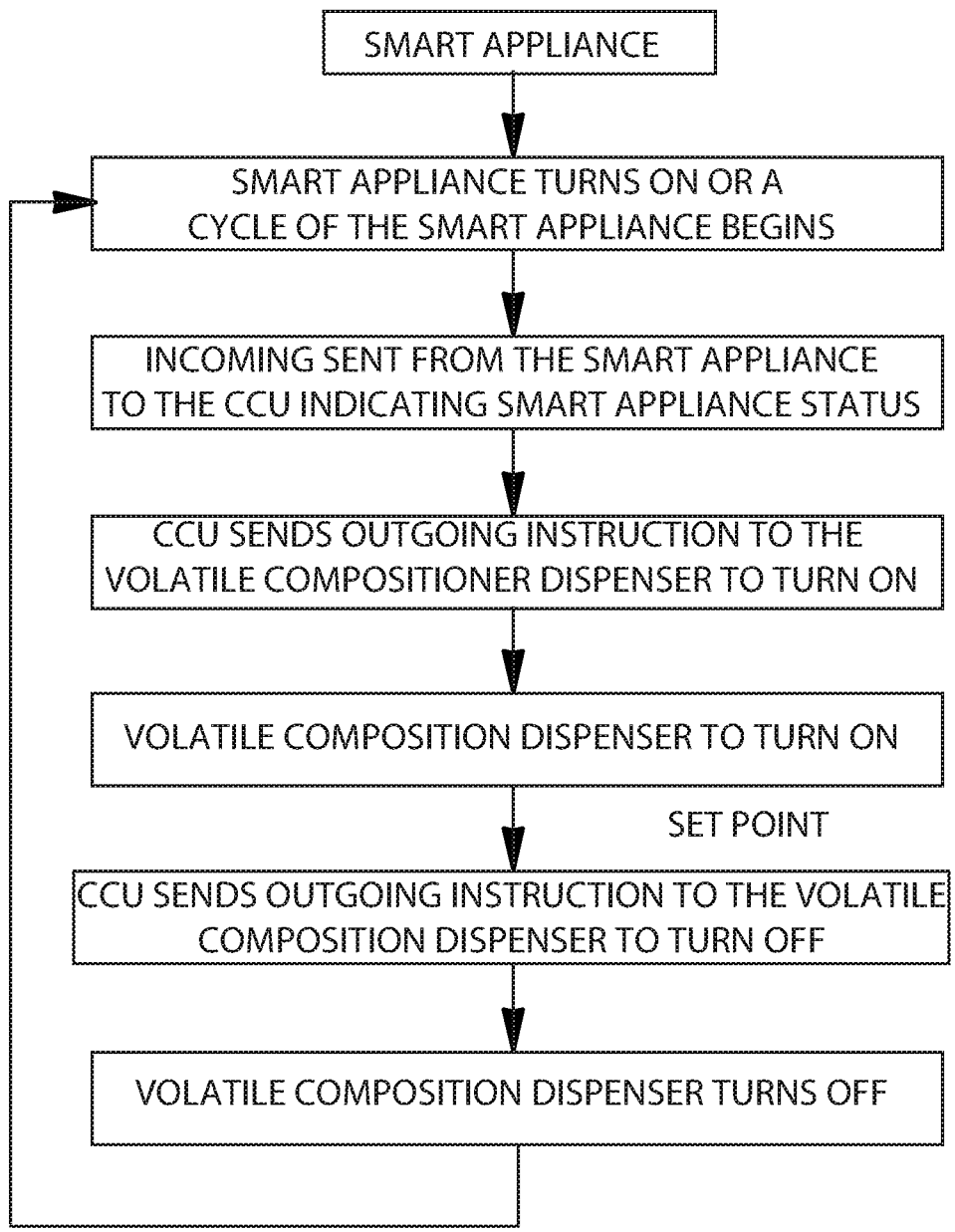
FIG. 6 illustrates an exemplary algorithm that may be used by the CCU to control the volatile composition dispenser and/or a smart appliance(s).

As discussed above, the CCU may be figured to run various algorithms that couple the operation of the volatile composition dispenser with the operation of the smart appliance. FIG. 6 illustrates an exemplary algorithm that may be used by the CCU 102 to control the volatile composition dispenser 104 and/or a smart appliance(s) 130. A smart appliance 130 may be communicably connected with the CCU 102. The smart appliance 130 may turn on either by manual control by the user or by an outgoing instruction sent from the CCU 102 to the smart appliance. The smart appliance 130 may be configured to turn ON or OFF using an algorithm set by the user, or the smart appliance 130 may be configured to be remotely turned ON or OFF by the user from a user interface on a computer or smart device, or the smart appliance 130 may be turned ON or OFF directly by the user on the smart appliance itself.

The smart appliance 130 may be configured to send an incoming signal to the CCU 102 whenever the smart appliance 130 is turned ON, whenever a particular cycle begins and/or ends, and/or when the smart appliance 130 is turned OFF. The algorithm may be configured to turn the volatile composition dispenser 104 ON after the smart appliance 130 is turned ON or after a cycle of the smart appliance 130 starts. Once the CCU 102 receives the incoming signal from the smart appliance 130 indicating the status of the smart appliance 130 that is set to cause the volatile composition dispenser 104 to turn ON, the CCU sends an outgoing instruction to the volatile composition dispenser 104 to turn ON. The volatile composition dispenser 104 may remain on until a set point occurs. For example, the algorithm may be configured to keep the volatile composition dispenser 104 ON for a predetermined amount of time, or for the duration of a cycle or multiple cycles of the smart appliance 130, or until the smart appliance 130 turns OFF. Once the programmed set point occurs, the CCU 102 sends an outgoing instruction to the volatile composition dispenser 104 to turn OFF. The algorithm may be repeated each time the smart appliance 130 turns ON or the particular cycle of the smart appliance 130 turns ON.

The algorithm may be programmed to turn the volatile composition dispenser ON after the smart appliance 130 is turned off. This algorithm may occur in addition to the algorithm described above with reference to FIG. 6, or may be run in alternative to the algorithm described above.

Set points may include a duration of time; a level of volatile composition dispensed; a current condition or status of a component, or the like. The processor may utilize various components in order to determine when a set point has been reached. For example, the processor may utilize a clock, which may be connected with the CCU or remotely located on a computer, smart device, or on the internet may be used to measure a duration of time. In another example, a sensor may be used to measure various conditions, such as the current temperature or level of volatile composition in the air. The sensor may be located on any component of the system or remote from the components of the system. The set point may also be based on a condition of a component. For example, a set point may be that a component is turned ON or OFF, which may signal the CCU to move on to the next step in the algorithm. The status of a component may be communicated to the CCU.

The set point used to control when the volatile composition dispenser is turned off may be a duration of time. The duration of time may be in the range of about 5 minutes to about 60 minutes, or in the range of about 10 minutes to about 30 minutes. The set point may also be the status of the smart appliance. For example, the set point may be when the smart appliance turns off or when a particular cycle of the smart appliance ends. The set point may be configured as a predetermined duration of time after the appliance is turned off or a predetermined duration of time after a cycle of an appliance ends.

The memory 124 may be configured to store multiple set points. For example, there may be different set points for different times, time periods of a day and there may be different set points for different days of the week. The processor may include a clock in determine which set point is to be used for a particular time of day and/or day of the week.

The processor may be configured to use outgoing signals or sensor measurements from different components located within a house or building at different times of the day and/or different days of the week. For example, a first volatile composition dispenser may be located in a first room of a house and may be coupled with a first smart appliance. In addition, a second volatile composition dispenser may be located in a second room of the house or in the same room as the first room and may be coupled with the operation of a second smart appliance that is different from the first smart appliance. The CCU may be programmed concurrently control the first and second volatile composition dispensers. The CCU may be programmed to control the first and second volatile composition dispensers whenever the first and second appliances are operating. The first and second smart appliance may run at the same time, different times, or at overlapping times.

The CCU may be configured as a thermostat such as the thermostat shown in FIG. 2. Power for the thermostat may be scavenged from the control wires that connect the air handling device to the thermostat. The thermostat may include a processor or memory, or the thermostat may communicate with a remote processor and/or memory. The thermostat may include a user interface. The thermostat may be a NEST® learning thermostat, a LUTRON® thermostat etc.

The processor may compute optimal set points from an algorithm based on user preferences of volatile composition levels and smart appliance operation profiles based on historical sensor measurements, historical set points, and known information on energy efficiency, comfort, and volatile composition levels. A machine learning algorithm can learn a user(s) preferred set points at various times of day and/or days of the week and/or can be used to program a more energy efficient algorithm, for example. An exemplary learning system is used in a NEST® learning thermostat. An exemplary learning system is also described in U.S. Pat. No. 9,115,908. The processor then transmits the optimal set points to the memory which then stores the set points for control of the HVAC.

Devices, including the air handling device, volatile composition dispenser, and/or smart appliance(s), of the system may interact with each other through the CCU such that events detected by one device may influence actions of another device or the current status of one device may influence actions of another device.

User Interface

The systems and methods of the present disclosure may include one or more user interfaces 108. The user interface 108 may be configured in various different forms. A user can interact with the user interface 108 to adjust set points as well as connect the sensors 106 through the CCU 102 for viewing of live sensor data on the user interface. The CCU 102 could also connect to the internet or intranet and pass through information, such as sensor measurements and the set points to a server for the purpose of remote monitoring on a user interface 108.

Figure 7:
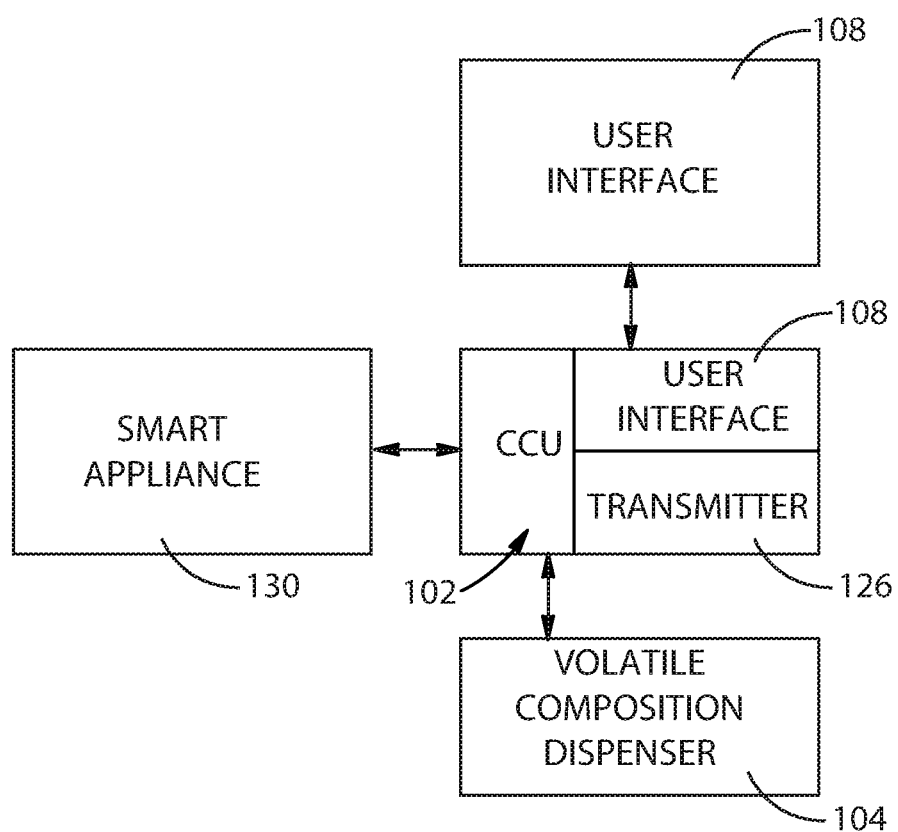
FIG. 7 illustrates an exemplary system having more than one user interface.

FIG. 7 illustrates an exemplary system having more than one user interface. In FIG. 7, a first user interface is connected with the CCU and a second user interface is a remote user interface. The remote user interface may be in the form of a computer or handheld smart device.

Where the CCU is configured as a thermostat, the thermostat may include a user interface where the user can adjust temperature set points by pushing buttons or turning dials, for example.

The user interface may be configured as a program, HTML website, or a Native application that is accessible by a user through a computer or handheld smart device. A handheld smart device may include an iPhone®, iPad®, or an Android® or Microsoft® based system. The user interface may be accessible on a computer such as a desktop, laptop, or tablet.

The system of the present disclosure may include a handheld smart device or computer that comprises the CCU 102, including the processor 122, memory 124, and/or user interface 108.

Air Handling System

The system 100 may include an air handling device. Air handling device includes a fan. The air handling device may provide heating, ventilation, air condition (HVAC) and/or air handling to an enclosure, such as a single-family home, apartment, office building, business, and the like. The air handling device 110 may be configured as a forced air type heating and cooling system. However, the air handling device may be configured in various different ways. For example, the air handling device may be configured in the form of a radiant heat based system; heat-pump based system; fan, including ceiling fan or portable fan; portable air conditioner; and/or portable heater.

The air handling device may have one or more controls. The controls on the air handling device may include turn ON/OFF the heater, turn ON/OFF the air conditioner, and/or turn ON/OFF the fan only. It is to be appreciated that the fan may also run when the heater or air conditioner is ON in order to push the heated or cooled air throughout the at least one room of the building.

The air handling device may include a wireless communication module in order to be wirelessly connected with various components of the system, such as the CCU, the volatile composition dispenser 104, and/or the smart appliance, through a wireless communication link.

Exemplary systems and methods that include coupling the operation of an air handling device with the operation of a volatile composition dispenser are described in U.S. patent application, entitled "SYSTEMS AND METHODS FOR COUPLING THE OPERATIONS OF AN AIR HANDLING DEVICE AND A VOLATILE COMPOSITION DISPENSER", Ser. No. 14/879,110, filed on Oct. 8, 2015. Exemplary systems and methods for controlling an air handling device with a volatile composition dispenser are described in U.S. patent application, entitled "VOLATILE COMPOSITION DISPENSER HAVING A TEMPERATURE SENSOR TO REMOTELY CONTROL AN AIR HANDLING DEVICE", Ser. No. 14/879,108, filed on Oct. 8, 2015.

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example a range disclosed as "1 to 10" is intended to mean "1, 2, 3, 4, 5, 6, 7, 8, 9, and 10." It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Values disclosed herein as ends of ranges are not to be understood as being strictly limited to the exact numerical values recited. Instead, unless otherwise specified, each numerical range is intended to mean both the recited values, any integers within the specified range, and any ranges within the specified range. For example a range disclosed as "1 to 10" is intended to mean "1, 2, 3, 4, 5, 6, 7, 8, 9, and 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system, comprising:
   a. a central communication unit;
   b. a one or more smart appliance component comprising a baby monitor; and
   c. a dispenser for modifying the environment in which the baby monitor exists;
   d. wherein the central communication unit, the baby monitor, and the dispenser are wirelessly connected to one another,
   e. wherein the central communication unit comprises a processor to control dispensing from the dispenser, and
   f. wherein the dispenser comprises a composition to assist with a state or condition selected from the group comprising sleep, wake, respiratory health, and combinations thereof,
   wherein the composition has a scent that matches a scent associated with sleep, waking, and/or respiratory health, and wherein the central communication unit is operating ON/OFF controls of the composition dispenser with the ON/OFF controls or the particular cycles START or END times of the one or more smart appliance.

2. The system of claim 1, wherein the baby monitor and/or central communication unit comprises a sensor to sense temperature.

3. The system of claim 1, wherein the baby monitor and/or central communication unit comprises a sensor to sense relative humidity.

4. The system of claim 1, wherein the wireless connection is via an ad hoc mesh network protocol.

5. A system, comprising:
   a. an environment modifying component;
   b. a smart appliance component comprising a baby monitor comprising a relative humidity sensor and a temperature sensor; and
   c. a central communication unit component, the relative humidity sensor and the temperature sensor sends sensor measurements to the central communication unit in the form of incoming signals;
   d. a user interface comprising a smart phone, the user interface displaying information received from the relative humidity sensor and the temperature sensor, wherein the received information is stored in a database to recommend optimum set points taking comfort and energy efficiency into consideration;
   e. wherein the environment modifying component, the smart appliance component, and the central communication unit component are communicably connectable; and
   f. wherein the central communication unit component controlling the environment modifying component with the information stored in the database.

6. The system of claim 5, wherein the central communication unit component controls the environment modifying component based on signals from the relative humidity sensor and the temperature sensor.

7. The system of claim 5, wherein setpoints of the environment modifying component can be adjusted via the user interface.

8. A system, comprising:
   a. a central communication unit;
   b. a one or more smart appliance component comprising a baby monitor; and
   c. a dispenser for modifying the environment in which the baby monitor exists;
   d. wherein the central communication unit, the baby monitor, and the dispenser are wirelessly connected to one another,
   e. wherein the central communication unit comprises a processor to control dispensing from the dispenser, and
   f. wherein the dispenser comprises a composition to assist with a state or condition selected from the group comprising sleep, wake, respiratory health,
   wherein the composition has a scent that matches a scent associated with sleep, waking, and/or respiratory health, and wherein the central communication unit is operating ON/OFF controls of the composition dispenser with the ON/OFF controls or the particular cycles START or END times of the one or more smart appliance.

* * * * *